US010071228B2

(12) United States Patent
Ollivier

(10) Patent No.: US 10,071,228 B2
(45) Date of Patent: Sep. 11, 2018

(54) PREFORMED STYLET FOR GUIDING A LEAD TO CONTACT THE SEPTUM

(75) Inventor: Jean-Francois Ollivier, Villers LeBacle (FR)

(73) Assignee: Sorin CRM SAS, Clamart (FR)

( * ) Notice: Subject to any disclaimer, the term of this patent is extended or adjusted under 35 U.S.C. 154(b) by 785 days.

(21) Appl. No.: 12/487,241

(22) Filed: Jun. 18, 2009

(65) Prior Publication Data

US 2010/0004662 A1     Jan. 7, 2010

(30) Foreign Application Priority Data

Jun. 20, 2008   (FR) ...................................... 08 03446

(51) Int. Cl.
 *A61M 25/09* (2006.01)
 *A61N 1/05* (2006.01)
 *A61M 25/00* (2006.01)

(52) U.S. Cl.
 CPC ............ *A61M 25/09* (2013.01); *A61N 1/056* (2013.01); *A61M 25/0041* (2013.01);
 (Continued)

(58) Field of Classification Search
 CPC ......... A61N 1/056–1/0575; A61N 2001/0578; A61M 25/09; A61M 25/0041;
 (Continued)

(56) References Cited

U.S. PATENT DOCUMENTS 3,521,620 A * 7/1970 Cook ................... A61B 1/0056
                                                        600/585
4,215,703 A * 8/1980 Willson .......... A61M 25/09033
                                                        600/585
(Continued)

FOREIGN PATENT DOCUMENTS

EP     0 778 044     12/1995
EP     0 778 044     11/1997
(Continued)

OTHER PUBLICATIONS

FR, Foreign Search Report (Annexe Au Rapport De Recherche Preliminaire; Ralatif A La Demande e Brevet Francais No. FR 0803446 FA 709328), dated Jan. 21, 2009.

*Primary Examiner* — Darwin Erezo
*Assistant Examiner* — Jonathan Hollm
(74) *Attorney, Agent, or Firm* — Foley & Lardner LLP

(57) ABSTRACT

Preformed guiding stylet for introducing a septal lead in contact with the septum or other intra-corporal device in contact with body tissue. This stylet includes a flexible wire to be introduced by its distal end in a central lumen of the lead, and a control handle. The wire is elastically deformable in bending and has sufficient rigidity in torsion to enable transmission by the handle rotation of a rotational movement over the entire length of the wire. Unstressed, the wire comprises successively in its distal part a first curvilinear portion a first straight portion a second curvilinear portion and optionally a second straight portion. The first and second curvilinear portions extend in respective planes making an angle between them defining a dihedral which axis comprises the first straight portion. The total length of the first curvilinear portion coincides with the anatomical curvature of the venous system.

20 Claims, 3 Drawing Sheets

(52) U.S. Cl.
CPC .......... *A61M 25/09016* (2013.01); *A61M 2025/09133* (2013.01); *A61M 2025/09175* (2013.01)

(58) Field of Classification Search
CPC .......... A61M 2025/09108–2025/09141; A61M 2025/09175
USPC .......... 606/108, 129; 600/585; 607/116, 119
See application file for complete search history.

(56) References Cited

U.S. PATENT DOCUMENTS

| | | | |
|---|---|---|---|
| 4,716,757 A | | 1/1988 | McGregor et al. |
| 4,719,924 A | * | 1/1988 | Crittenden ...... A61M 25/09033 600/434 |
| 4,867,174 A | * | 9/1989 | Skribiski ........................ 600/585 |
| 4,925,445 A | * | 5/1990 | Sakamoto et al. ............. 604/528 |
| 4,940,062 A | * | 7/1990 | Hampton ........ A61M 25/09033 600/434 |
| 5,476,500 A | * | 12/1995 | Fain et al. ..................... 607/126 |
| 5,640,955 A | * | 6/1997 | Ockuly et al. ................. 600/374 |
| 5,658,327 A | | 8/1997 | Altman et al. |
| 5,728,148 A | * | 3/1998 | Bostrom et al. ............... 607/116 |
| 5,759,202 A | * | 6/1998 | Schroeppel .................... 607/126 |
| 5,807,324 A | * | 9/1998 | Griffin, III ..................... 604/529 |
| 5,807,339 A | | 9/1998 | Bostrom et al. |
| 5,810,746 A | * | 9/1998 | Goldstein et al. ............. 600/585 |
| 5,837,007 A | | 11/1998 | Altman et al. |
| 5,868,700 A | | 2/1999 | Voda |
| 5,897,584 A | * | 4/1999 | Herman ........................ 607/122 |
| 5,902,331 A | * | 5/1999 | Bonner et al. ................ 607/122 |
| 6,066,126 A | * | 5/2000 | Li et al. ........................ 604/532 |
| 6,254,550 B1 | * | 7/2001 | McNamara et al. .......... 600/585 |
| 6,385,492 B1 | | 5/2002 | Ollivier et al. |
| 6,408,214 B1 | | 6/2002 | Williams et al. |
| 6,944,506 B1 | * | 9/2005 | Morgan et al. ............... 607/122 |
| 7,056,294 B2 | * | 6/2006 | Khairkhahan et al. ....... 600/585 |
| 7,462,184 B2 | | 12/2008 | Worley et al. |
| 2002/0169377 A1 | * | 11/2002 | Khairkhahan et al. ....... 600/433 |
| 2002/0193811 A1 | * | 12/2002 | Chan ............................. 606/148 |
| 2003/0208220 A1 | * | 11/2003 | Worley et al. ................ 606/190 |
| 2004/0116878 A1 | * | 6/2004 | Byrd ..................... A61N 1/056 604/263 |
| 2004/0243209 A1 | * | 12/2004 | Jarl et al. ...................... 607/119 |
| 2006/0122682 A1 | | 6/2006 | Somer et al. |
| 2009/0071012 A1 | | 3/2009 | Shan et al. |

FOREIGN PATENT DOCUMENTS

| | | |
|---|---|---|
| EP | 0993840 | 4/2000 |
| EP | 1 920 795 | 5/2008 |
| EP | 2039390 | 3/2009 |
| WO | WO 91/15152 | 10/1991 |
| WO | WO 94/20165 | 9/1994 |
| WO | WO 02/04062 | 1/2002 |
| WO | WO 2005/082445 | 9/2005 |

* cited by examiner

PREFORMED STYLET FOR GUIDING A LEAD TO CONTACT THE SEPTUM

FIELD OF THE INVENTION

The present invention relates to a stylet for use in the introduction of intracorporeal leads, including detection/stimulation leads associated with "active implantable medical devices" as such devices are defined by the Jun. 20, 1990 directive 90/385/CEE of the European Communities Council, and more particularly a lead associated with implants for cardiac stimulation, re-synchronization, cardioversion and/or defibrillation. The present invention relates more specifically to the implantation of the particular type of intracardiac lead known as a "septal lead" that is intended to be placed against the inter-ventricular or inter-atrial wall, defined as the "cardiac septum".

BACKGROUND OF THE INVENTION

Intracorporeal leads are in particular used with multisite pacing or re-synchronization devices, to stimulate the left atrial and/or ventricular cavities, depending on the configuration and the location of the lead. These leads are typically equipped with a screw anchor, generally a retractable screw, allowing fixing of the lead head into the wall of the septum, so that the electrode of the distal part of the lead is applied in a manner substantially perpendicular to the wall. Given this setup, the placing of the septal leads is a particularly delicate operation—unlike the placement of right cavity pacing leads which are simply pushed until they reach the apex of the right ventricle. The septal leads are, like the other intracardiac leads, introduced through the venous network, either via the right cephalic vein and the superior vena cava ("right approach"), or via the left cephalic vein and the superior vena cava ("left approach"). In the case of a conventional right cavity pacing lead, the lead is simply pushed to the apex of the ventricle. However, for a septal lead, once the head has reached inside the cavity, the lead distal termination needs to be oriented perpendicularly to the septum wall and pressed against the wall at the selected pacing site so that it can be anchored there by screwing the lead head, including the electrode, into the septum.

To easily guide the distal end at the time of implantation to the selected pacing site, and in a direction substantially perpendicular to it, the lead must be relatively rigid. To do this, the surgeon first introduces a stylet in the form of flexible wire into the hollow, flexible sheath, of the lead body. The stylet is provided at its proximal end, emerging from the lead, with a control handle allowing the surgeon to transmit a rotation and translation movement of the stylet within the sheath. The lead, rigidified by the stylet, can then be introduced in the venous network. Then its distal termination can be oriented by rotation of the handle at the proximal termination of the stylet. In this way, the surgeon rotates the end of the lead head—which presents a curve—and directs it to the septum implant site. Once the site is reached, the surgeon then anchors the lead head by rotation of the screw anchor that penetrates the tissues of the septal wall.

In contrast to right cavity pacing leads, whose positioning is relatively easy (in the ventricle apex), in the case of a lead head to be anchored to the septal wall, the diversity of venous access routes and the cardiac morphology render difficult both the access to the septum and the positioning of the lead head against the septum wall.

To accommodate these features, surgeons attempt to define their own distal conformation of the stylet, by imposing a plastic deformation of the distal end thereof, so as to give the corresponding end of the lead, once inserted into the cavity, a curve facilitating the approach to and docking against the septal wall.

The patent EP1920795A1 (and its corresponding U.S. patent publication US20090105724) describes a stylet having a distal end that consists of an elastic thread preformed using a special three-dimensional configuration, comprising a succession of curved arches facing in different levels. Once the stylet is inserted in the lead, and the stylet/lead combination is introduced into and deployed in the ventricle, this particular configuration allows giving the lead such a shape that it turns naturally in the desired direction. The fine tuning of the distal lead head positioning will be reached by pushing more or less the control handle located at the proximal termination of the stylet. Because of the succession of the various curved arches, the stylet axial movement inside the lead will be transformed in a spontaneous rotation of the latter, without the need to apply and to transmit a torque. Indeed, in this device, the proximal portion is made of a permanently deformable material (so as to give a "memory" to the shape of the stylet), which is not designed to transmit the torque due to its relative plasticity. It is also noteworthy that in this system, all curved conformations of the stylet (and thus of the lead) is located, and used, in the right ventricle, that is to say inside the heart, for the purpose is to enable a fine tuning of the orientation of the lead head by an axial translation of the stylet.

The patent EP 0 778 044 A2 (and its corresponding U.S. Pat. No. 5,807,339) describes an accessory of the "guide-wire" or wire guide type, adapted to a particular technique called Over-The-Wire (OTW), in which the guide wire crosses through a probe sheath along its entire length, leading and emerging at the distal end. In reaching its non traumatic end, and to enable its progress directly into a vein safely, the wire guide is terminated at its distal end with a ball or a spire. While returning more or less the guide wire in the probe sheath, it is possible to stiffen it and give it a particular, alterable, curvature to orient more easily in the heart chamber or into the coronary network (but always in the part located inside the heart). A typical application of such a guide wire is the placement of a lead into the coronary sinus by a technique consisting of both to penetrate the core in the coronary sinus and then into the coronary venous system, by gradually sliding the lead over the guide until the final position is obtained.

More complex devices have also been proposed, with two stylets fitting into one another, allowing changing the opening angle of the curved part of the distal end. This solution is relatively expensive and complex, and often unsuitable for the intended function, as it is only possible to change the opening angle of the curved end, not the radius of curvature itself.

In addition, whatever the device used, a typical phenomenon that is well known to physicians during the rotation of the stylet within the hollow shaft of the lead is that, given a gradual rotation of the handle at the proximal end of the stylet, the rotation is translated to the opposite distal end, first by a very gradual rotation of the distal end of the stylet, and, second, after a certain threshold, a sudden jump in rotation of the stylet distal end as the gradual rotation of the handle of the stylet continues. This mechanical relaxation phenomenon results from a progressive accumulation of mechanical torque of the stylet in the lead sheath, followed by a sudden release of these constraints with a jump at the distal end. The jump is felt by the physician in the form of a "clicking" or "rattling" during a rotation of the stylet. This results in an inability to finely control the movement of the distal part of the stylet, and thus correctly directs the lead toward the septum with the required progression and precision.

The origin of this rattle phenomenon is the position of mechanical torque equilibrium of the stylet into the lumen of the hollow shaft of the lead, the latter taking the shape of the venous network in which it was inserted. Insofar as the insertion of the lead, rigidified by the stylet, often leads to permanent deformation of the stylet body, although small, this permanent deformation systematically tries to integrate in the path imposed by the venous morphology (which itself depends on the path, right or left), because of the basic mechanical principle of least energy in torsion.

OBJECT AND SUMMARY OF THE INVENTION

It is therefore an object of the invention to propose a new technique for providing self-positioning of a septal lead based on the anatomy of venous access and, consequently, an efficient transmission of torque created by a control handle, through to the distal end of the septal lead, for easy placement of the lead head against the wall of the septum, towards a given stimulation site chosen by surgeon.

It should be understood, however, that although the invention is described here in the context of the placement of a probe, it also equally applies to the placement of other intercorporeal devices, including the placement of a transeptal catheter, for example, to achieve access to a left cavity.

Broadly, the present invention is directed to an improved guide stylet of a type generally known, e.g., as disclosed by EP 1 920 795 A1 above, comprising a flexible wire to be introduced by its distal end in a central lumen of the lead, and a control handle attached to wire at its proximal end. The wire is elastically deformable in bending and its torsion has sufficient rigidity to enable transmission over the entire length of the wire of a movement by rotation of the control handle at the proximal end. In an unstressed condition, the wire comprises at its distal end, successively, a first curvilinear portion, a first straight portion, and a second curvilinear portion.

In accordance with the present invention, the first curvilinear portion and the second curvilinear portion extend in respective planes which define between them a dihedral angle, which axis includes the first straight portion. The total length of the first curvilinear portion, the first straight portion, and the second curvilinear portion is preferably between 82 and 195 mm, this dimension being selected in order to coincide with the anatomical curvature of the venous network in which the lead equipped with its stylet will be introduced.

In other words, advantageously, instead of fighting against the phenomenon of accumulation of mechanical torque constraints and a sudden release resulting from the mechanical principle of least energy in torsion, i.e., the rattling action, the invention proposes to use this simple and predictable mechanical phenomenon, to ensure positioning of the lead head in the direction of the septum.

Indeed, the particular conformation given to the stylet, according to the invention, allows making it mechanically coincide with the curvature of the venous system, including the superior vena cava and the cephalic vein (right or left). This curvature, which is naturally included in the anatomical curvature, can automatically steer the distal end of the stylet, and thus the lead head, in the desired direction. The angle may be finely adjusted by rotating the handle of the stylet, with a range of flexibility in the order of ±20° to ±40°, carried out gradually around the equilibrium torque position, before the mechanical jump (rattling) of the stylet occurs.

The solution proposed by the invention is particularly advantageous because it is simple and economical to implement, unlike the complex dual-stylet systems that have been proposed in the prior art.

In addition, the stylet of the present invention can be preformed directly in the factory, because it only requires a fine adjustment by the surgeon (plastic deformation of the distal end). In other words, the overall conformation is produced by the manufacturer and then refined by the surgeon during implantation. The final adjustment will mainly involve adjusting the distal end, while the other curves (radius, angle, position on the length of the mandrel, angular drawings of curves, etc.) are adjusted during manufacturing.

In an alternative embodiment, the stylet is not preformed, but simple conformation tools usable in surgery are made available to the surgeon, for example, thermoformed templates with different radii of curvature built into on the "blister" packaging in which the stylet is packaged, with appropriate angular benchmarks.

In general, as appropriate, the first curvilinear portion and the second curvilinear portion can be configured in relation to one another, and the first straight portion, so as to extend away from each other, on opposite sides of a half-plane containing the first straight portion, for a stylet designed to be introduced into the venous system via the right cephalic vein, or in mutual alignment, in the same side of a half-plane containing the first straight portion, for a stylet designed to be introduced into the venous system via the left cephalic vein. The control handle then, preferably, comprises a marking, e.g, an R or L or a color coding indicating whether the stylet is a stylet for the introduction into the venous system via the right cephalic vein or the left cephalic vein.

According to various preferred embodiments:
  the dihedral angle is preferably less than 45°, and advantageously selected from between 10° and 30°;
  The first curvilinear portion has a radius of curvature that is less than or equal to 200 mm, and more preferably between 40 and 60 mm;
  The first curvilinear portion has a curvilinear opening angle of at least 100, and more preferably between 70° and 110°;
  The first straight portion has a length of at least 10 mm, and more preferably between 30 and 70 mm;
  The second curvilinear portion has a radius of curvature selected from between 10 and 15 mm;
  The second curvilinear portion presents a curvilinear opening angle selected from between 20° and 40°; and
  the wire optionally also presents in its distal end, after the second curvilinear portion, a second straight portion of length less than or equal to 15 mm.

Yet additional aspects of the present invention are directed towards a kit and a system including a stylet for guiding the introduction of a probe wire into the venous system, so that the direction and guidance of the distal end of a probe touches the wall of the atrium or ventricular septum.

Such a kit or system preferably may include an already preformed wire, according to a configuration as described above. Alternatively, it may include a not preformed wire, i.e., a wire that is essentially straight in the unstressed state, and a template for forming the wire according to a pattern as described above, said template being possibly a relief formed in the stylet packaging.

BRIEF DESCRIPTION OF THE DRAWINGS

Further features, advantages and characteristics of the present invention will now be described in accordance with the following detailed description of preferred embodiment is of the invention, made with reference to the drawings annexed, in which the same numerical references designate items that are identical or functionally similar from one figure to the next, and in which.

DETAILED DESCRIPTION OF THE INVENTION

Figure 1:
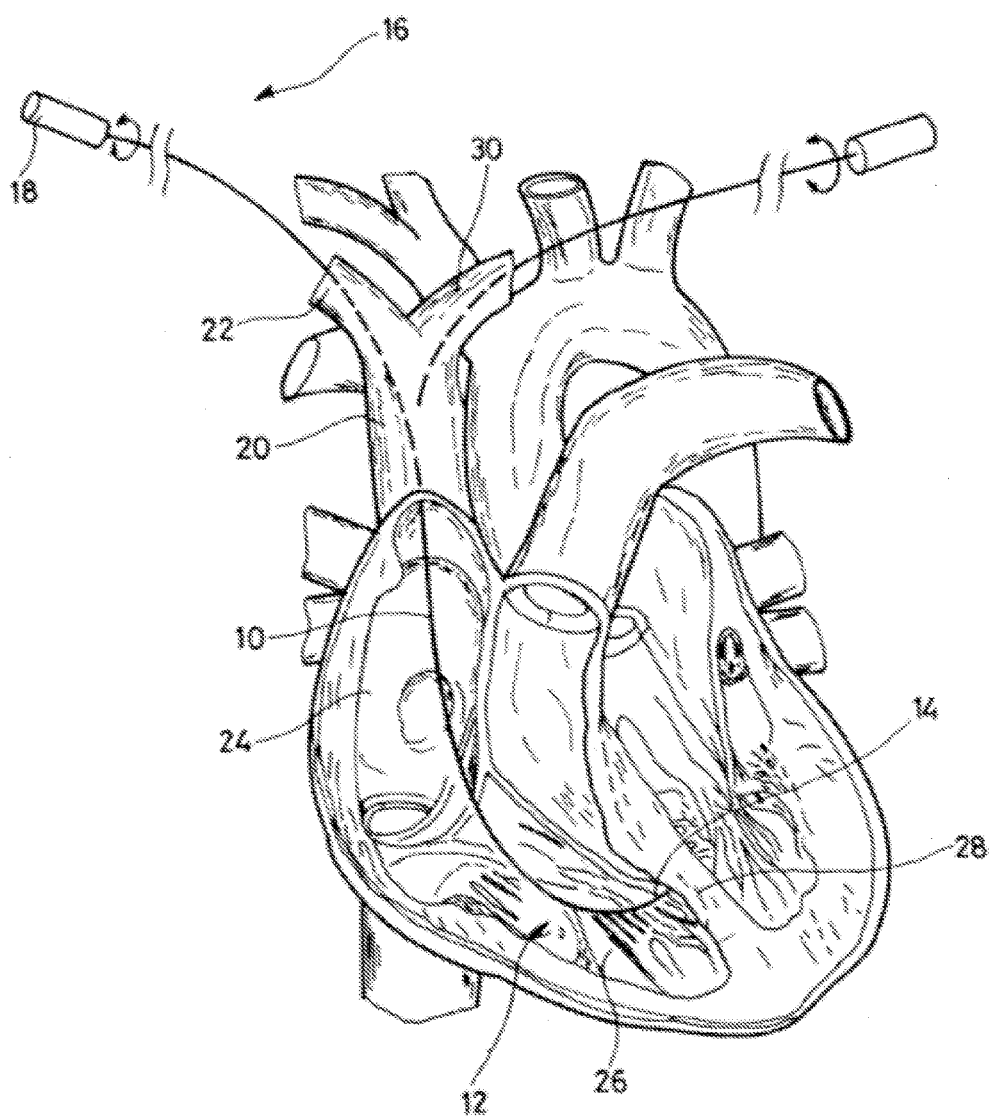
FIG. 1 schematically illustrates the pathways and the mode of implantation of a lead placed against the cardiac septum.
Figure 2:
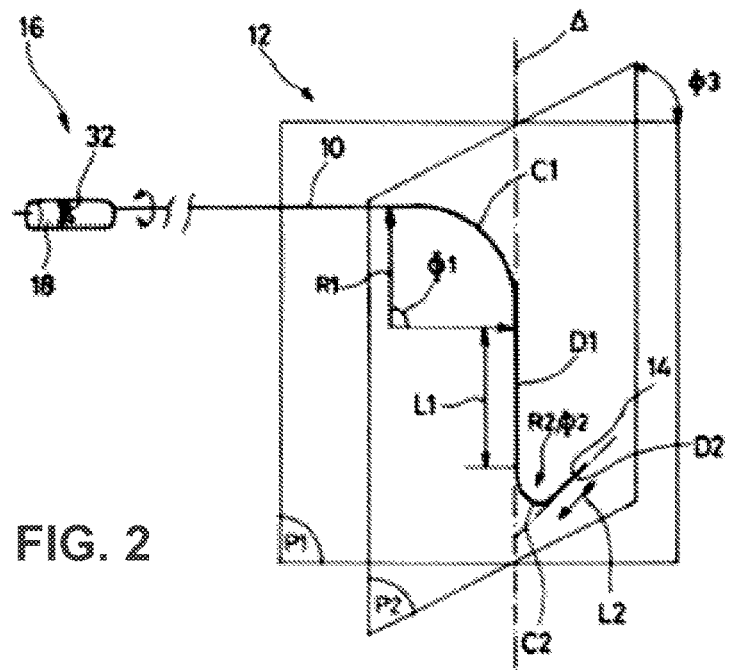
FIGS. 2 and 3 illustrate a stylet according to the invention, for implantation respectively in a right approach and a left approach.
Figure 3:
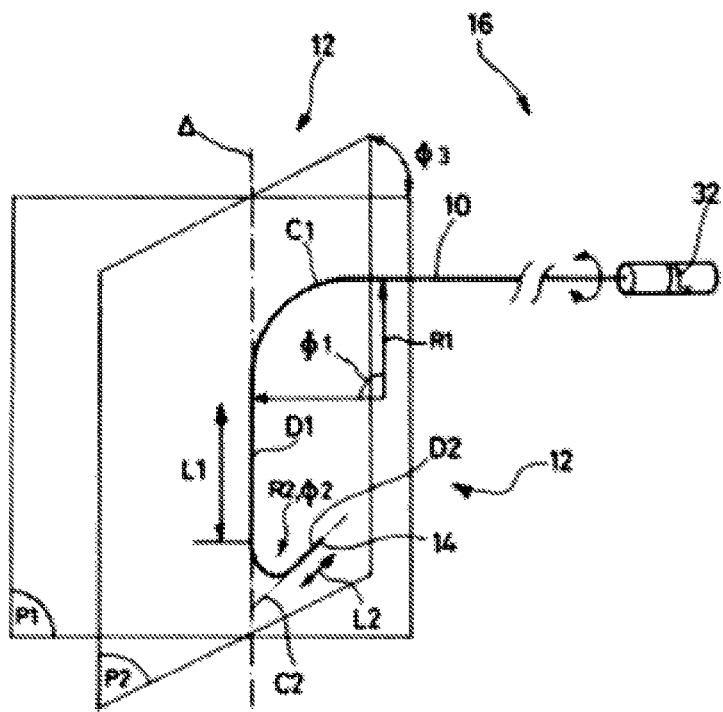

With reference to FIGS. 1 to 3, reference 10 generally designates a stylet threaded into the lumen of the central hollow shaft of an intracardiac lead so that the latter, which structure is very flexible, replicates the form given by the stylet introduced inside.

The distal part 12 and the distal end 14 arrives in the right ventricle and corresponds to the lead head, which is intended to be implanted against the interventricular wall or septum (noting that the invention also could be applied to a location against the interatrial septum).

At the opposite end, proximal portion 16, the stylet 10 is provided with an actuating control handle 18 which allows control by torsion transmission effort of the distal end 12 (14) to guide it, and therefore the lead in which the stylet is threaded into, in the direction of the selected pacing site.

Stylet 10 is preferably made of a flexible material that is relatively rigid but elastically deformable, such as a stainless steel wire AISI 302 or AISI 304 of diameter typically between 0.30 mm and 0.45 mm. The wire is elastically deformable in bending, torsion and has a sufficient rigidity to allow transmission of the rotational movement, controlled by the surgeon through the handle 18, over the length of the thread.

The lead provided with stylet 10 is inserted into the heart chamber via the superior vena cava 20 and the right cephalic vein 22 to reach the right atrium 24 and ventricle 26 (in the case of an implantation against the inter-ventricular septum). By rotating the handle 18, the surgeon then directs the lead head in the direction of the interventricular septum 28 to the wall of the septum, where he can then anchor the lead head by screwing it into the septum tissue. An alternate approach is possible via the cephalic vein and 30 left superior vena cava 20. The latter case is called "left approach," while the former case is called "right approach". FIGS. 2 and 3 illustrate the particular conformation given to the distal part 12 of the stylet 10 according to the invention. This configuration is different depending on the selected approach, FIG. 2 corresponding to a right approach and FIG. 3 to a left approach.

The specific left or right approach conformation is preferably given to stylet 10 during manufacturing. Stylet 10 is thus supplied preformed, so as to present a curvature that, as will be described when it is deployed in the so-called free state, i.e., in the absence of any stress (e.g., especially before the introduction in the central lumen of the hollow shaft of the lead).

The distal part 12 comprises successively, from the central part to the distal end 14:

A first curvilinear portion C1, having a first radius of curvature R1 and opening angle ϕ1

A first straight portion D1 having a first length L1;

A second part curvilinear portion C2, having a second radius of curvature R2 and opening angle ϕ2, and, optionally A second straight portion D2 having a second length L2.

It can be noted that, in the illustrated example, the curvilinear portions may be an arc, i.e., having a constant radius of curvature, or other curved form, including a curved arc of ellipse, or a non-uniform radius of curvature. In the context of the present invention, the term "curvilinear" should be understood in its broadest, nonlinear sense.

Preferably, the curvilinear portions C1 and C2 are not coplanar, but rather arranged in two respective planes P1, P2 forming between them a angle ϕ3 defining a dihedral which axis Δ includes the first straight portion D1.

In the case of a stylet 10 for a right approach (FIG. 2), both curvilinear portions C1 and C2 are extended away from each other, i.e., on either side of a half-plane containing the straight part D1. In the case of a stylet for a left approach (FIG. 3), both curvilinear portions C1 and C2 are arranged in mutual alignment, i.e., on the same side of a half-plane containing the straight part D1.

If the stylets 10 are preformed during manufacturing, the packaging may contain both types of stylets, and the surgeon may then choose the one that is adapted to the selected approach, right or left, as appropriate. In this case, it is advantageous to provide the handle 16 with a marking 32, e.g., an "L" or "R" or a color code to more easily distinguish the two stylets.

In accordance with one embodiment of the present invention, the shape of the stylet may comprise one or more of the following seven parameters which vary within the following exemplary and non-limiting ranges:

For the first curvilinear portion: R1≤200 mm, preferably R1=40 to 60 mm

ϕ1≥100, preferably 70° to 110°

For the first straight part:

L1≥10 mm, preferably 30 to 70 mm

For the second curvilinear portion:

R2=10 to 15 mm

ϕ2=20° to 40°

For the second straight part:

L2=0 to 15 mm (which means that the second straight part may be omitted (L2=0), the distal end 14 located immediately to the former free end of the second curvilinear portion C2)

Mutual angle of plane P1 and P2:

ϕ3=0° to 45°, preferably 10° to 30°.

Taking the extreme values of curvature and angle, one can calculate the length of the arc developed curvilinear contact:

for the first curvilinear portion C1: 49 to 115 mm, for the second curvilinear portion C2: 3 to 10 mm.

Or, with a length of straight portion D1 between 30 and 70 mm and a length of a second straight portion (optional) between 0 and 15 mm, a total development between:

82 and 195 mm in the absence of a second straight portion, and 82 to 210 mm in the presence of a second straight portion.

These extreme values of developed length reflect the fact that a succession of rectilinear and curvilinear portions must cover the anatomical curvature of the venous network in which the lead will be introduced provided with its stylet, and not the heart chamber (where only the second straight and curved portions are spread).

One skilled in the art will recognize that the present invention can be practiced by other than the embodiments disclosed herein, and the particular exemplary parameters given, which are provided for purposes of illustration and not of limitation.

Figure 4:
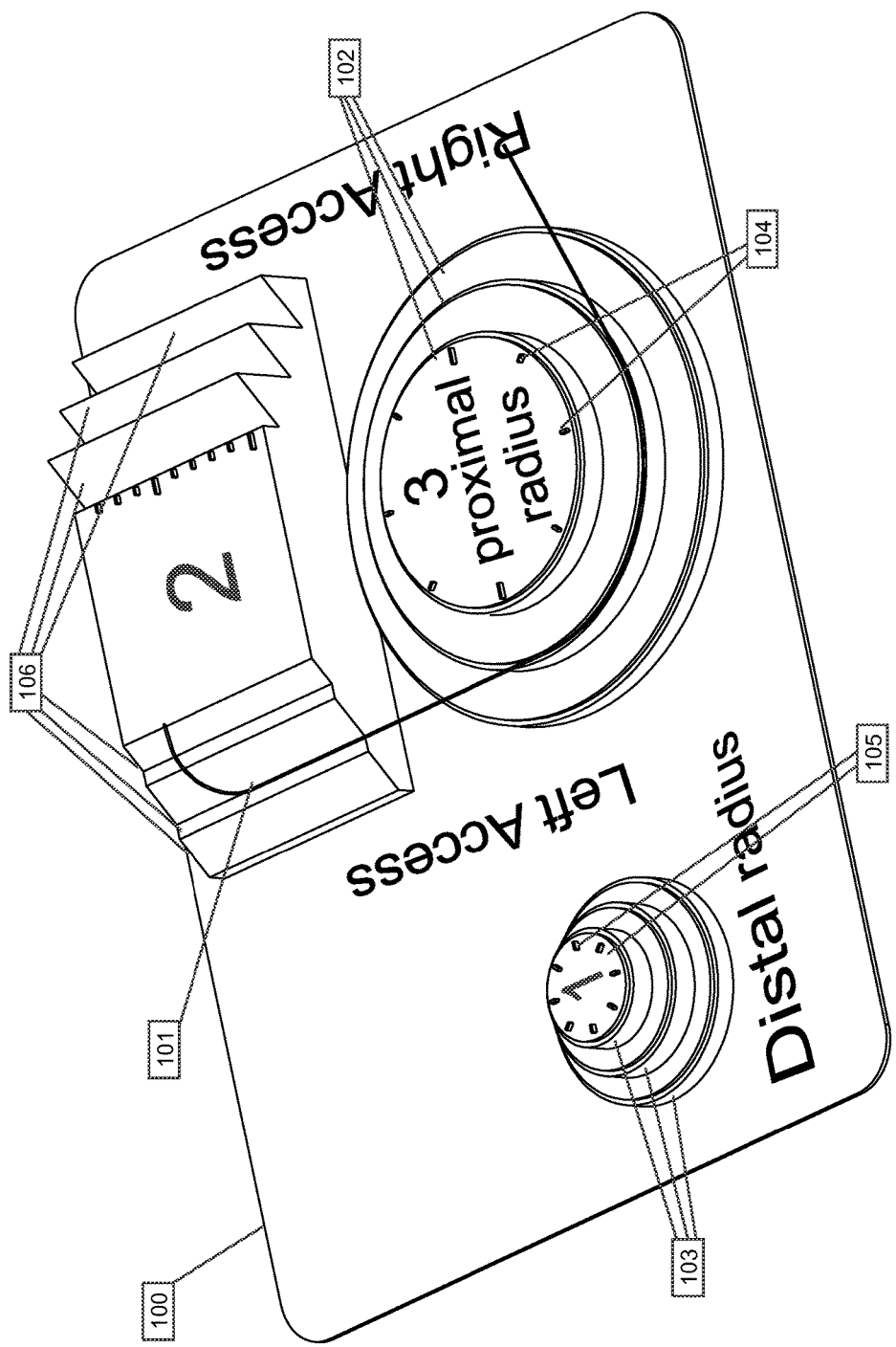
FIG. 4 illustrates a kit according to the invention, of a template for forming the shape of a wire according to a desired pattern.

Referring to FIG. 4, in an alternative embodiment in which the stylet is not preformed, a simple conformation tool template 100 is made available to the surgeon. Thermoformed template 100 allows the wire to be shaped with different radii of curvature built into on the "blister" packaging in which the stylet is packaged to bend wire 101 into the proper radius R1 102 and R2 103. Different angular benchmarks are provided to allow proper orientation of angles Φ1 104, Φ2 105, and Φ3 106.

I claim:

1. A guiding stylet, for introducing a septal lead to contact an atrial or ventricular septum wall, comprising:
    a flexible wire having a proximal end and a distal end suitable for passage in a central lumen of said septal lead, and
    a control handle fixed to the proximal end of the wire and rotatable about an axis;
    said wire being elastically deformable in bending and having in an unstressed state, at its distal end, an unstressed shape comprising, successively: a first curvilinear portion, a first straight portion, and a second curvilinear portion nearer to the distal end of the wire than the first curvilinear portion;
    wherein the wire has a rigidity in torsion to allow transmission along its length of a rotational movement by a rotation of the handle, whereby the rotational movement of the wire by a rotation of the handle causes an adjustment of an opening angle of the second curvilinear portion by accumulating torque in the wire;
    wherein the first curvilinear portion and the second curvilinear portion extend in respective planes that make an angle between them that define a dihedral angle that includes the first straight portion, wherein the dihedral angle is less than 45°;
    wherein the total length of the first curvilinear portion, the first straight portion, and the second curvilinear portion is between 82 and 195 mm;
    wherein said distal end is configured to be positioned within an anatomical curvature of a venous system extending from a right or left cephalic vein, through a superior vena cava, and towards the septum wall;
    wherein the distal end comprises a positioned shape when positioned within the anatomical curvature; and
    wherein the positioned shape substantially matches the unstressed shape.

2. The stylet of claim 1, wherein the first curvilinear portion and the second curvilinear portion are configured in relation to one another and the first straight portion to extend away from each other on opposite sides of a half plane containing the first straight portion, said stylet being designated to be introduced into the venous system via the right cephalic vein.

3. The stylet of claim 2, wherein the control handle further comprises a marking indicating that said stylet is designated to be introduced inside the venous system via the right cephalic vein.

4. The stylet of claim 1, wherein the first curvilinear portion and the second curvilinear portion are configured in relation to another and the first straight portion to extend in mutual alignment on the same side of a half-plane containing the first straight portion said stylet being designated to be introduced into the venous system via the left cephalic vein.

5. The stylet of claim 4, wherein the control handle further comprises a marking indicating that said stylet is designated to be introduced inside the venous system via the left cephalic vein.

6. The stylet of claim 1, wherein the wire further comprises a second straight portion positioned distal of the second curvilinear portion.

7. The stylet of claim 6, wherein the second straight portion further comprises a length less than or equal to 15 mm.

8. The stylet of claim 1, wherein the dihedral angle is between 10° and 30°.

9. The stylet of claim 1, wherein the first curvilinear portion has a radius of curvature less than or equal to 200 mm.

10. The stylet of claim 9, wherein the first curvilinear portion has a radius of curvature between 40 and 60 mm.

11. The stylet of claim 1, wherein the first curvilinear portion provides an opening angle of at least 10°.

12. The stylet of claim 11, wherein the first curvilinear portion provides an opening angle of between 70° and 110°.

13. The stylet of claim 1, wherein the first straight portion has a length of at least 10 mm.

14. The stylet of claim 13, wherein the first straight portion has a length between 30 and 70 mm.

15. The stylet of claim 1, wherein the second curvilinear portion has a radius of curvature between 10 and 15 mm.

16. The stylet of claim 1, wherein the opening angle is adjustable between 20° and 40°.

17. A kit for the introduction into the venous system, and for the direction and guidance of the distal end of a probe until contact with the wall of the atrial or ventricular septum, comprising:
    a preformed guiding stylet according to the configuration of claim 1.

18. A guiding stylet, for introducing a septal lead to contact an atrial or ventricular septum wall, comprising:
    a flexible wire having a proximal end and a distal end suitable for passage in a central lumen of said septal lead, and
    a control handle fixed to the proximal end of the wire and rotatable about an axis;
    said wire being elastically deformable in bending and having in an unstressed state, at its distal end, an unstressed shape comprising, successively: a first curvilinear portion, a first straight portion, and a second curvilinear portion nearer to the distal end of the wire than the first curvilinear portion;
    wherein the wire has a rigidity in torsion to allow transmission along its length of a rotational movement by a rotation of the handle, whereby the rotational movement of the wire by a rotation of the handle causes an adjustment of an opening angle of the second curvilinear portion by accumulating torque in the wire;
    wherein the first curvilinear portion and the second curvilinear portion extend in respective planes that make an angle between them that define a dihedral angle that includes the first straight portion, wherein the dihedral angle is between 10° and 30°;

wherein the first curvilinear portion has a radius of curvature between 40 and 60 mm and provides an opening angle of between 70° and 110°;

wherein the second curvilinear portion has a radius of curvature between 10 and 15 mm, and wherein the second curvilinear opening angle is adjustable between 20° and 40°;

wherein the total length of the first curvilinear portion, the first straight portion, and the second curvilinear portion is between 82 and 195 mm;

wherein the first straight portion has a length between 30 and 70 mm;

wherein said distal end is configured to be positioned within an anatomical curvature of a venous system extending from a right or left cephalic vein, through a superior vena cava, and towards the septum wall;

wherein the distal end comprises a positioned shape when positioned within the anatomical curvature; and wherein the positioned shape substantially matches the unstressed shape.

19. The stylet of claim 18, wherein the wire further comprises a second straight portion positioned distal of the second curvilinear portion.

20. The stylet of claim 19, wherein the second straight portion further comprises a length less than or equal to 15 mm.

* * * * *